United States Patent [19]

Jewett

[11] Patent Number: 4,936,316
[45] Date of Patent: Jun. 26, 1990

[54] METHOD AND APPARATUS FOR INDICATING PARTURITION

[75] Inventor: Warren Jewett, Cary, N.C.

[73] Assignee: Sonodyne America Limited, Morrisville, N.C.

[21] Appl. No.: 231,833

[22] Filed: Aug. 3, 1988

[51] Int. Cl.⁵ .............................................. A61B 5/10
[52] U.S. Cl. .................................... 128/775; 128/778; 340/573
[58] Field of Search ................ 128/774, 775, 778, 788; 340/573

[56] References Cited

U.S. PATENT DOCUMENTS

| | | | |
|---|---|---|---|
| 4,147,160 | 4/1979 | Aranew et al. | 128/775 |
| 4,232,686 | 11/1983 | Kammlade, Jr. | 128/775 |
| 4,319,583 | 3/1982 | Ingle | 128/775 |

Primary Examiner—Max Hindenburg
Assistant Examiner—J. P. Lacyk
Attorney, Agent, or Firm—Kane, Dalsimer, Sullivan, Kurucz, Levy, Eisele and Richard

[57] ABSTRACT

An animal birth detector is described comprising apparatus attached in the proximity of the animal's vulva for detecting the birth of offspring by monitoring the swelling of the vulva during the period prior to and during delivery of the newborn. More specifically, the animal birth detector comprises a unitary device containing a transmitter attached to the skin proximate one side of the animal's vulva, the transmitter utilizing a reed relay switch to sense the proximity of a permanent magnet located in the device. As the vulva dilates at time of delivery, the magnet is moved out of the magnetic field sensing area of the reed switch, turning on the transmitter whose transmissions are received by a receiver monitored by an attendant.

7 Claims, 1 Drawing Sheet

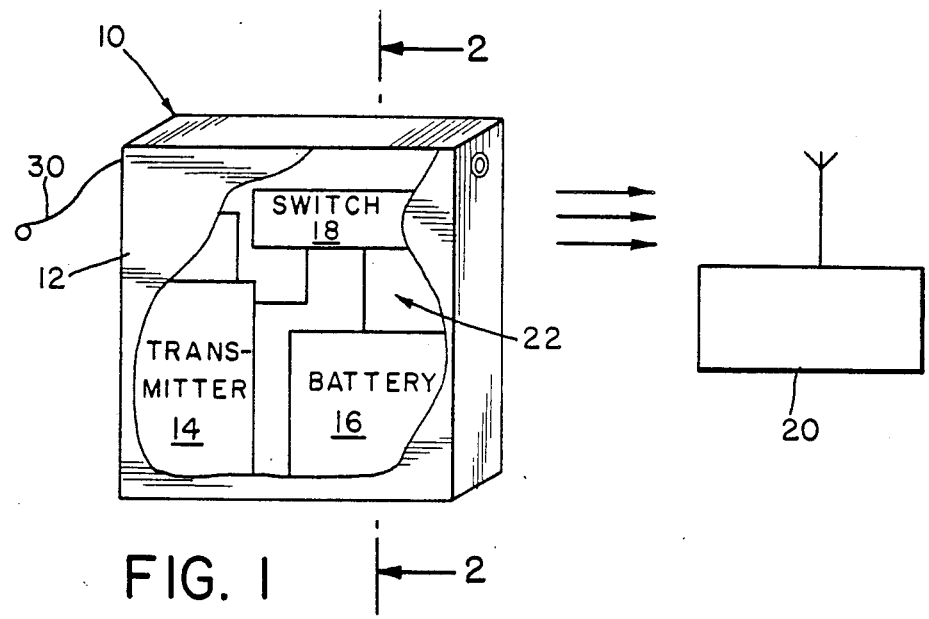
FIG. 1
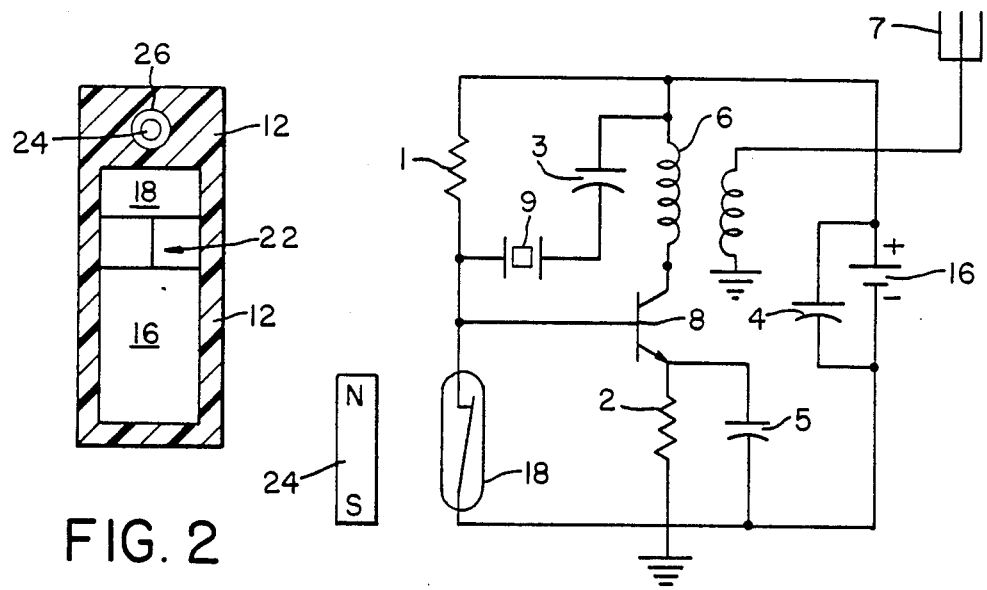
FIG. 2
FIG. 3

METHOD AND APPARATUS FOR INDICATING PARTURITION

BACKGROUND OF THE INVENTION

1. Field of the Invention

The invention concerns methods and devices to indicate when an animal is giving birth to its young.

2. Brief Description of the Prior Art

It will be appreciated that when horses, cattle, swine, and other animals give birth to their offspring, complications may develop which require the aid of the stockman or the veterinarian to prevent death of the newborn or for that matter, the mother. If the animal is not penned, it is common for the animal to attempt to hide during the birthing, complicating the problem of aiding the birth.

With the values which have been placed upon animals today in such cases as racehorses, milk cows, zoo specimens and the like, it is usual for an attendant to remain close to the animal at all times during the expected period of birthing. This may require maintaining all night vigils.

Obviously then, it is to the attendant's advantage to know exactly when, and if necessary, where an animal is, when the process of birthing begins.

The prior art literature is replete with descriptions of devices and methods for detecting the birth of newborn animals. For example, in the U.S. Pat. No. 4,232,686, apparatus for detecting the onset of parturition comprises three separate components to be mounted in three specific and different locations in respect to the vaginal orifice of the pregnant animal. Such apparatus has obvious limitations under certain circumstances. For example, an assemblage of the component parts in the proper locations is required. Unless this is accomplished properly, there is a high probability of a false triqgering of the indicator, or inoperability.

Also, the prior art apparatus such as the above-described prior art apparatus, may be difficult to assemble in the proper position, because its structure does not take into account the handedness of the individual making the assembly. For example, it can be fabricated to facilitate assembly by a right-handed or a left-handed individual, but not by both such individuals. Although this may sound like a trivial advantage, imagine a left-handed individual attempting to assemble apparatus designed for a right-handed operator, on the buttocks of a nervous 2,000 lb. animal.

Another disadvantage associated with prior art devices for monitoring parturition in pregnant females, particularly devices which include a switch and a remote control such as a bar magnet, is the occasional false triggering of a transmission (signal). The magnet must be placed within a certain range proximity to the switch to inhibit energizing the electrical circuit for a signal transmission. It is movement of the magnet component outside of the range of operation which closes the circuit. Unless one uses a very powerful magnetic force (usually equated with a large magnetic mass), the range of the remote control will be small and the distance between the reed switch and the magnet critically short, for maintaining the switch in an open position. A few millimeters distance can mean the difference between opening and closing the switch. False triggering of the signal can occur from simple movements of the animal, resulting in displacement of the magnet outside of the control range. This is particularly true for very active zoo animals or horses which are prone to rub against fixed objects to relieve the sensory perception associated with the presence of the device. The device of the present invention solves this disadvantage of the prior art, without increasing the mass of the magnet. The solution we found comprises placement of the magnet component as a remote control device, in a fixed position relative to the switch mechanism and immobile under ordinary conditions apart from actual parturition. False triggering of a signal is thus obviated.

Other advantages of the device of the invention will be apparent to those skilled in the art from the following description.

SUMMARY OF THE INVENTION

The invention comprises a device for detecting parturition in a female animal; which comprises;

a signal transmitter;

a source of electrical power for activating the signal transmitter;

electrical circuit means between the signal transmitter and the power source;

a switch in the circuit means for energizing and de-energizing the circuit, said switch being operable by a remote control means;

an enclosure means for the sealed containment of the transmitter with the power source, the circuit means and the switch within a closed chamber;

said enclosure means including an open-ended bore having no communication with the chamber, for mounting therein the remote control means;

remote control means, the presence of which in a position within the bore, will maintain the switch in a de-energized circuit position and the absence of which from a position within the bore will maintain the switch in a circuit energizing position; and means connected to the remote control means for removal of said remote control means from the bore by parturition.

BRIEF DESCRIPTION OF THE DRAWINGS

FIG. 1 is a view-in-perspective of an embodiment device of the invention, partially cut-away to show internal components and its schematic relationship to a signal receiver.

FIG. 2 is a view along lines 2—2 of FIG. 1.

FIG. 3 is an electrical schematic diagram of an embodiment radio transmitter circuit.

DETAILED DESCRIPTION OF THE PREFERRED EMBODIMENTS OF THE INVENTION

A complete understanding of the invention may be had from the following description of a preferred embodiment device of the invention when read in conjunction with a viewing of the accompanying drawings of FIGS. 1-3, inclusive.

Referring first to FIG. 1, a device 10 of the invention is seen in perspective, partly cut-away to view internal components. Hermetically sealed and contained within a moisture-proof housing or enclosure 12 is an electrical circuit which includes a miniature radio transmitter 14 including its associated antenna for transmission of a given radio signal. The transmitter 14 is powered by a conventional electrical energy source such as replaceable dry cell battery 16. The battery 16 is electrically connected to the transmitter 14 through a switch 18 for opening and closing the circuit. When the switch 18 closes the circuit, the circuit is energized and transmitter 14 is activated to generate and transmit a radio signal which may be detected by the remotely placed radio receiver 20. The receiver 20 can also be miniaturized so it may be carried on the person of the individual who will monitor for the signal indicating parturition. Receipt of the radio signal causes receiver 20 to emit a loud beep or other audible tone to warn the farmer, stockman, veterinarian or like concerned individual that parturition has occurred.

The individual who is monitoring the receiver 20, is alerted by the transmitted signal. The frequency of the transmitted signal is such that a direction finding antenna may be utilized in combination with the receiver 20 to point out the general direction in which the animal is located. The individual then may seek out the animal and ascertain that the newborn and the mother are in satisfactory condition or require assistance.

Transmitter 14 and receiver 20 are both of common design such as may be found in a conventional paging system. Since transmitter 14 is only activated during parturition, the life of battery 16 is spared, and therefore transmitter 14 and battery 16 may be reused numerous times. This is an economic advantage.

The housing or enclosure 12 of the device 10 contains as a single unit, all of the transmitter, battery, circuitry and switches required to generate and transmit a predetermined signal upon the occurrence of parturition, as will be described more fully hereinafter. The enclosure 12 hermetically seals the interior components within a chamber 22 to protect them from dirt, moisture, and like contamination which could interfere with desired operation of the device or shorten its useful operating life. Representative of materials which can be employed to fabricate enclosure 12 are polymeric resins such as polyvinyl chloride, polypropylene, polyurethane, polycarbonate and the like.

In the preferred device 10, the switch 18 is a reed relay switch which, in the presence of magnet 24, opens and thus inhibits energization of the transmitter 14 and signal transmission. Upon the removal of magnet 24 from the proximity of reed switch 18, the switch 18 closes and the transmitter 14 is energized and commences signal transmission. Since the reed switch 18 is a magnetic field proximity device, when the magnet 24 is more than about 10 cm. from reed switch 18, the reed switch 18 does not respond to the now distant magnetic field and remains closed.

It should be appreciated from the drawings of FIGS. 1 and 2 that the magnet 24 is a bar magnet held in a fixed position relative to switch 18 by an interference fit within bore 26. In this way, the magnet 24 is also at least partially embraced within the enclosure of enclosure 12 and thus protected. The bore 26 traverses a thickened end of the enclosure 12 and is open at both ends to receive the inserted magnet 24. This openness of bore 26 facilitates cleaning thereof when magnet 26 is removed. Although the magnet 24 is wholly mounted and contained within the body of enclosure 12 it is physically separated and sealed apart from the chamber 22 so that its removal from bore 26 does not leave an access opening to the chamber 22 or its contents. The magnet 24 functions as a remote control means for operating switch 18, although it is integral to the device 10, which is a unitary, compact and portable device. The magnet 24 functions to operate switch 18 by its presence or removal from the bore 26. The magnet 24 may be removed from bore 26 by pulling on the flexible thong 30, which is attached to one end of the bar magnet 24 (attachment not shown in FIG. 1). When removed from the bore 26, by pulling on thong 30, the switch 18 closes and activates the electrical circuit to energize the transmitter 14.

FIG. 2 is a cross-sectional view along lines 2—2 of FIG. 1 and shows further structural details of the device 10.

FIG. 3 is a schematic diagram of an embodiment radio transmitter circuit which is advantageously used in the device 10 of FIG. 1. The following components may be utilized in its construction: resistor 1, 47K ohm; resistor 2, 560 ohm; capacitor 3, 36 pf; capacitors 4, 5, 1000 pf; battery 16, 1.5 volt, S-13 Eveready battery; transformer 6, sub-miniature, 16 turn (capacitor 3 side), 2 turn (antenna 7 side); transistor 8, MMT 74, Motorola; switch 18, reed switch, mini-25-11S, Hamlin; magnet 24 ¼ inch by 1 inch, Samarium-Cobalt alloy; quartz crystal 9, 49.850 MHz, SC-45, Sentry Manufacturing Co., Chickasha, Okla.

In use, the device 10 including the bar magnet 24 inserted in bore 26 may be held in proximity to the animal's vulva by an adhesive or suture attached vinyl pouch adapted to hold the device 10 in a pouch formed therein. The pouch is adhered to the animal's skin by adhesive means or suturing of the pouch in place in proximity to the vaginal orifice. The free end of the thong 30 may be similarly attached to the animal, but in a position proximate to the opposite side of the animal's vaginal orifice. The attachment of the pouch holding enclosure 12 and the attachment of the free end of thong 30 to the animal should be made to provide enough slack in thong 30 so that normal movements of the animal will not take up the slack and pull magnet 24 from bore 26, effecting a false triggering of the device 10.

When parturition occurs, the vulva expands and the slack in thong 30 is taken up, pulling the magnet 24 from bore 26, thereby remotely activating the switch 18. Optimal degrees of slack in thong 30 will differ for different animals and the range of normal movements of the associated musculature, etc. Those skilled in the art of animal attendance will appreciate or can learn from trial and error, appropriate degrees of slackness for the particular animal.

The free end of the thong 30 may similarly attached to the animal, but in a position proximate to the opposite side of the animal's vaginal orifice.

It is suggested that the skin surrounding the vulva be cleansed with a cleaning material, such as warm soapy water, rinsed and dried before attachment of device 10. If excess hair is present which might interfere with the adhesion of the pouch to the skin, it may be desirable to clip or shave this hair off. It is also suggested that tincture of benzoine be applied to the area where the pouch will be placed prior to the placement. This is for the purpose of making the area antiseptic prior to the placement, especially by suturing.

Representative of adhesives which may be used are 3M Ostomy Seal, however, especially on large animals, suturing is preferred to secure the device 10 in its place.

What is claimed is:

1. A device for detecting parturition in a female animal, which comprises an electrical circuit including:
   a signal transmitter;
   a source of electrical power for activating the signal transmitter;

and a switch means electrically connecting the signal transmitter to the power source;

said switch means for energizing and de-energizing the circuit, said transmitter being activated by energizing the circuit;

remote control means for operating said switch;

an enclosure means for the sealed containment of the transmitter with the power source, and the switch within a closed chamber;

said enclosure means including an open-ended bore having no communication with the chamber, for mounting therein the remote control means;

whereby said remote control means, the presence of which in a position within the bore, will maintain the switch in a de-energized circuit position and the absence of which from a position within the bore will maintain the switch in a circuit energizing position; and means connected to the remote control means having one end extending externally from said device for removal of said remote control means from the bore by parturition.

2. A device as set forth in claim 1 wherein the switch is a reed switch and the remote control means is a magnet.

3. A device as set forth in claim 1 wherein the enclosure is moisture-proof.

4. A device of claim 1 wherein the mounting of the remote control means in the bore is by a sliding frictional fit.

5. A device of claim 1 wherein the power source is a replaceable dry cell.

6. A device of claim 1 wherein the means for removal of the remote control means comprises a thong.

7. A method of detecting parturition in a pregnant female animal, which comprises;

providing a device, which comprises an electrical circuit including;

a signal transmitter;

a source of electrical power for activating the signal transmitter;

and a switch means electrically connecting the signal transmitter to the power source;

said switch means for energizing and de-energizing the circuit, said transmitter being activated by energizing the circuit;

remote control means for operating said switch;

an enclosure means for the sealed containment of the transmitter with the power source, and the switch within a closed chamber;

said enclosure means including an open-ended bore having no communication with the chamber, for mounting therein the remote control means;

whereby said remote control means, the presence of which in a position within the bore, will maintain the switch in a de-energized circuit position and the absence of which from a position within the bore will maintain the switch in a circuit energizing position;

means connected to the remote control means having one end extending externally from said device for removal of said remote control means from the bore by parturition;

attaching said device on one side of the animal's vulva;

attaching the one end of the means for removal on another side of the animal's vulva;

whereby parturition will activate the means for removal to remove the remote control means from the mounting;

providing a radio receiver tuned to receive a signal from the signal transmitter; and monitoring the radio receiver for receipt of said signal.

* * * * *